(12) United States Patent
Cohen et al.

(10) Patent No.: US 7,792,334 B2
(45) Date of Patent: Sep. 7, 2010

(54) LOCATING BLOOD VESSELS

(75) Inventors: Robert F. Cohen, Kensington, MD (US); David Tumey, Germantown, MD (US); Scott McDermott, Washington, DC (US)

(73) Assignee: Immersion Corporation, San Jose, CA (US)

( * ) Notice: Subject to any disclaimer, the term of this patent is extended or adjusted under 35 U.S.C. 154(b) by 233 days.

(21) Appl. No.: 12/059,132

(22) Filed: Mar. 31, 2008

(65) Prior Publication Data

US 2009/0245601 A1 Oct. 1, 2009

(51) Int. Cl.
*G06K 9/00* (2006.01)
(52) U.S. Cl. ...................................... 382/115
(58) Field of Classification Search ................ None
See application file for complete search history.

(56) References Cited

U.S. PATENT DOCUMENTS

| | | | | |
|---|---|---|---|---|
| 5,787,185 | A * | 7/1998 | Clayden | 382/115 |
| 6,301,375 | B1 * | 10/2001 | Choi | 382/115 |
| 6,353,753 | B1 | 3/2002 | Flock et al. | |
| 6,447,460 | B1 | 9/2002 | Zheng et al. | |
| 7,158,660 | B2 * | 1/2007 | Gee et al. | 382/128 |
| 2003/0018271 | A1 | 1/2003 | Kimble | |
| 2006/0020212 | A1 | 1/2006 | Xu et al. | |
| 2006/0079750 | A1 | 4/2006 | Fauci et al. | |

FOREIGN PATENT DOCUMENTS

| | | |
|---|---|---|
| JP | 09294706 | 11/1997 |
| JP | 2006-098340 * | 4/2006 |
| WO | WO 01/82786 A2 | 11/2001 |
| WO | WO 2007/115570 A1 | 10/2007 |

OTHER PUBLICATIONS

English Abstract of JP 2006-098340, Osamu, Apr. 13, 2006, 1 page.*
English translation of JP 2006-098340, Osamu, Apr. 13, 2006, 14 pages.*
"Moving the Needle: Georgia Tech Researchers Develop Portable 'Vein Finder' for Faster, More Accurate Injections," Jan. 16, 2006, http://gtresearchnews.gatech.edu/newsrelease/vein-finder.htm.

* cited by examiner

*Primary Examiner*—Brian P Werner
(74) *Attorney, Agent, or Firm*—Medler Ferro PLLC

(57) ABSTRACT

Several systems and methods for locating blood vessels are described in the present disclosure. One of the implementations of a blood vessel locating system comprises an image capture device and processing circuitry. The image capture device is configured to capture a first image of a region of the skin of a subject when the region is illuminated by a first light and to capture a second image of the region of the skin when the region is illuminated by a second light. The processing circuitry is configured to calculate the difference between the first image and the second image to obtain a differential image. The processing circuitry is further configured to enhance the differential image to obtain an enhanced image of blood vessels located under the surface of the skin of the subject.

23 Claims, 6 Drawing Sheets

LOCATING BLOOD VESSELS

TECHNICAL FIELD

The present disclosure generally relates to locating blood vessels. More particularly, the present disclosure relates to illuminating the surface of a portion of the skin with certain types of light in order to locate the position of blood vessels under the skin.

BACKGROUND

In the medical field, blood vessels of a patient are often accessed for the purpose of drawing samples of blood, administering medicine through an IV inserted in a vein, inserting a catheter, etc. In order to access the blood vessels, medical professionals usually locate blood vessels by simply inspecting the surface of the skin of the patient under normal lights. Unfortunately, many attempts may be required to properly insert a needle or other instrument into blood vessels in this manner, which can cause unnecessary discomfort, and even sometimes pain, for the patient.

Some solutions have been proposed to assist medical professionals to locate a blood vessel under the skin of a patient. One device, referred to as a vein locator, uses an imagining technique to locate veins. The device then projects an image representing the veins on the outside surface of the subject's skin. However, this device is very expensive and is rather bulky. Another solution includes emitting an infrared light on the surface of the skin. The light in this device is reflected by the tissues, but absorbed by the blood vessels. By illuminating the skin in this way, the blood vessels can be more easily detected. Although these and other devices and solutions have assisted medical professionals to better locate blood vessels, further development is this regard can still be made, particularly to overcome the shortcomings of the prior art with respect to cost and portability.

SUMMARY

The present disclosure describes systems and methods for determining the location of blood vessels embedded under the skin of a subject. Of the numerous embodiments described herein, one embodiment of a blood vessel locating system comprises an image capture device and processing circuitry. The image capture device is configured to capture a first image of a region of the skin of a subject when the region is illuminated by a first light. The image capture device is also configured to capture a second image of the region of the skin when the region is illuminated by a second light. The processing circuitry is configured to calculate a difference between the first image and the second image to obtain a differential image. The processing circuitry is further configured to enhance the differential image to obtain an enhanced image of blood vessels located under the surface of the skin of the subject.

Other features, advantages, and implementations of the present disclosure, not expressly disclosed herein, will be apparent to one of ordinary skill in the art upon examination of the following detailed description and accompanying drawings. It is intended that such implied implementations of the present disclosure be included herein.

BRIEF DESCRIPTION OF THE DRAWINGS

The components in the following figures are not necessarily drawn to scale. Instead, emphasis is placed upon clearly illustrating the general principles of the present disclosure. Reference characters designating corresponding components are repeated as necessary throughout the figures for the sake of consistency and clarity.

DETAILED DESCRIPTION

Figure 1:
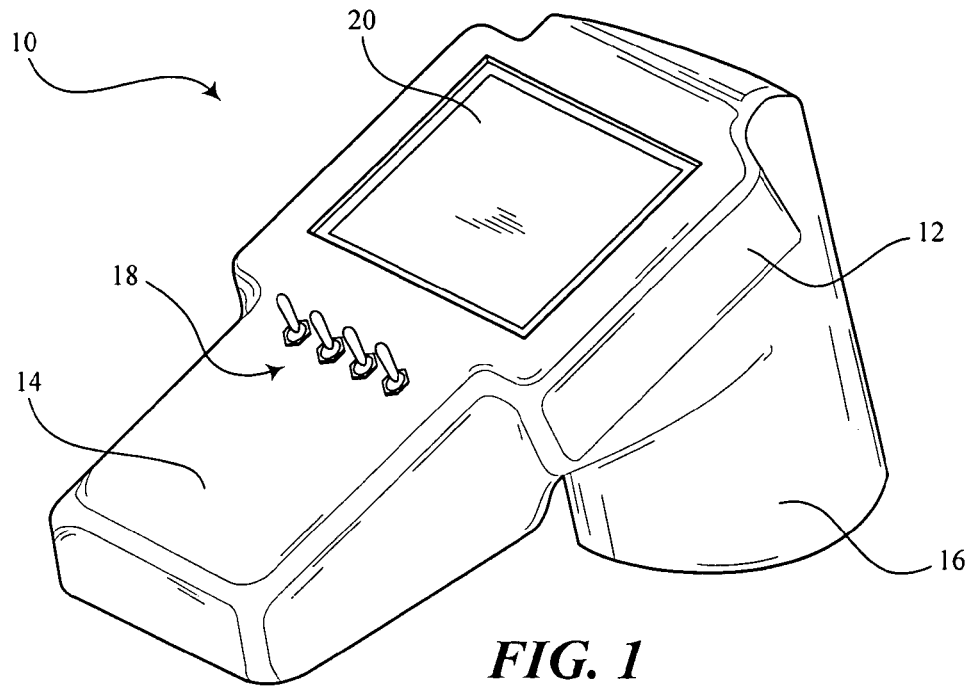
FIG. 1 is a diagram illustrating a blood vessel locating device according to one embodiment.

In the blood of humans and animals, hemoglobin carries oxygen from the lungs to other parts of the body. The oxygen is then released from the blood to the body tissues as needed, and the oxygen-depleted blood travels back to the lungs, where the blood is replenished with oxygen. During respiration, oxygen binds with the heme protein to form oxy-hemoglobin, which is the oxygen-loaded form of hemoglobin. When the oxygen is released, the deoxy-hemoglobin form is produced.

Oxy-hemoglobin naturally contains specific light absorption and light reflection characteristics depending on the wavelength of light. Deoxy-hemoglobin also contains its own specific light absorption and reflectivity characteristics with respect to light wavelength. It is noted, however, that when light at a wavelength of approximately 880 nm is emitted, the light absorption and reflection characteristics of both oxy-hemoglobin and deoxy-hemoglobin are about the same. At this wavelength, though, light does not experience absorption but experiences either transmission or reflection from other body tissue, such as the tissue in the vicinity of the blood vessels. Light that is transmitted through some layers of tissue is reflected by deeper tissue. The reflection characteristics of body tissue at 880 nm are about the same as its reflection characteristics under regular light in the visible spectrum.

By illuminating the skin with infrared light at approximately 880 nm, the tissue will normally reflect the light, while the blood vessels, containing either oxy-hemoglobin or deoxy-hemoglobin, absorb the light, thereby making the location of the blood vessels appear darker. Since 880 nm is in the infrared range, it cannot be seen by the human eye. However, many image sensors, such as charge coupled devices (CCDs) or complementary metal-oxide semiconductor (CMOS) imaging devices, are responsive to infrared light. Thus, the procedure of illuminating skin with infrared light can be used to make the blood vessels visually stand out with respect to the surrounding tissue.

As discussed in the present disclosure, an infrared light is emitted onto the skin and an image of the skin is taken. This image taken under the infrared light slightly distinguishes the blood vessels from the surrounding tissues. Imaging techniques, such as contrast enhancement, brightness leveling, and edge sharpening, may be used to optimize this image for subsequent processing. In order to further enhance the distinctions between blood vessels and tissue, a second image is captured using light within the visible light spectrum. The visible light may be in the blue-green region, for example, and may have a wavelength of approximately 470 nm. Since light in the visible spectrum, particularly bluish light, tends to be reflected by tissue and blood vessels, the visibility of the blood vessels in an image captured under this light is greatly reduced. This second image may also be optimized for subsequent processing, such as by smoothing or blurring to remove skin surface features that may be more apparent under the visible light.

Although the terms "visible light", "visible spectrum", etc. are used throughout the present disclosure, it should be noted that the type or frequency range of these lights may actually include any suitable wavelength or range that is different from the infrared light spectrum and does not necessarily require light that is visible to humans. However, for the sake of simplicity and consistency, the terms visible light, visible spectrum, etc. are used herein.

With the two images, an image processing device of the present disclosure subtracts one image from the other to obtain a differential image, which tends to highlight the location of the blood vessels and substantially eliminate the image of the skin and tissues. This differential image is then enhanced to make the image even more distinctive. For example, one enhancement technique may include colorizing the differential image. After enhancement of the differential image, the enhanced image is added to the original image captured under regular or visible light. The resulting image is therefore an even greater representation of the location of blood vessels. Knowing the location of blood vessels, a medical professional is better able to access the blood vessels to draw blood, insert an IV, insert a catheter, etc.

FIG. 1 is a diagram illustrating an embodiment of a blood vessel locating device 10. In this embodiment, blood vessel locating device 10 includes a housing 12 that supports electrical circuitry therein (not shown in FIG. 1). A portion of housing 12 includes a handle 14 allowing blood vessel locating device 10 to be held within a user's hand. In this sense, blood vessel locating device 10 is easily transportable and easy to manipulate.

Blood vessel locating device 10 also includes an open-ended enclosure 16, which in this implementation includes a circular cross-section forming a cylindrical tube. In other embodiments, enclosure 16 may have any reasonable shape or cross-section and may be located in other positions and orientations relative to handle 14. Although not shown in FIG. 1, enclosure 16 contains light sources, which can be supported along the interior surface of enclosure 16. At least a first set of light sources in enclosure 16 is capable of emitting light having a shorter wavelength than infrared light, such as light within a spectrum that is normally visible to a human eye. A second set of light sources is capable of emitting light within a near infrared (near IR) spectrum, which includes a wavelength range from 700 nm to 1.4 µm. Enclosure 16 may include one or more diffusing mechanisms configured to diffuse the light from the light sources in order to eliminate bright spots and to create a substantially uniform illumination pattern on the skin.

Also residing within enclosure 16 is an image capture device, such as, for example, a camera, one or more CCDs or CMOS devices, or other suitable device for detecting an image. Enclosure 16 may serve to maintain a minimum distance from the image capture device to the skin to accommodate the focal length of the image capture device. Enclosure 16 also serves to reduce the ambient light from external light sources. In addition to the embodiment of FIG. 1, housing 12 and enclosure 16 may include any design or configuration as desired. For example, blood vessel locating device 10 may be configured as a pocket scanner, a pen-shaped detecting device, etc.

Blood vessel locating device 10 also includes input devices 18 and a display screen 20. In this embodiment, input devices 18 are shown as toggle switches, but in other embodiment, input devices 18 may include other suitable types of data entry or selection devices as well. In use, input devices 18 may function to allow a user to enter information regarding the wavelength of light that is emitted from the light sources. The four switches shown in FIG. 1 may include, for example, one switch for selecting white light, one for selecting blue light, one for red light, and another for infrared. Input devices 18 may also allow entry of other information and/or selections as needed. Display screen 20 is configured to display a final image, as described in more detail below, representing the location of blood vessels. Images shown on display screen 20 are presented in real time or after a reasonably short delay. Images can be processed and displayed at about 30 frames per second or at any other suitable rate.

In operation, blood vessel locating device 10 is placed near a portion of a subject's skin where embedded blood vessels are to be located. Particularly, the subject may be a human patient in a clinical or medical setting. In other embodiments, the subject may be an animal or pet under the care of a veterinarian. For proper operation in a veterinary setting, modifications to blood vessel locating device 10 may be made if necessary. Blood vessel locating device 10 is held such that the open end of enclosure 16 is directed toward the section of the subject's skin that is to be observed. A small stand may be used in conjunction with or incorporated with blood vessel locating device 10 such that the user can access the skin while blood vessel locating device 10 is positioned a short distance from the skin. Depending on the user's settings and inputs, such as those related to input devices 18, blood vessel locating device 10 emits a first light in the visible spectrum and captures a first image of the skin when illuminated with the first light. Blood vessel locating device 10 also emits a second light in the near IR spectrum and captures a second image of the skin when illuminated with the second light. It should be noted that the order of illumination of the different lights can be reversed.

Processing circuitry within blood vessel locating device 10 processes the images individually and then obtains a differential image by calculating the difference between the first image associated with the visible light and the second image associated with the near IR light. This differential image is then enhanced, such as by colorizing the image, increasing the contrast of the image, darkening the image, and/or other suitable enhancement procedures. The processing circuitry then superimposes the enhanced image on the first image, which is associated with the visible light, to obtain a final image. This final image is then displayed on display screen 20. It should be understood that the operation of blood vessel locating device 10 can include any order of steps and may differ from the sequence discussed above. For instance, emission of the two different lights can occur in the reverse order. Also, the order of the image processing actions involving individual processing, calculating differences, subtraction, enhancement, and superimposing can be altered depending on the particular design.

Figure 2:
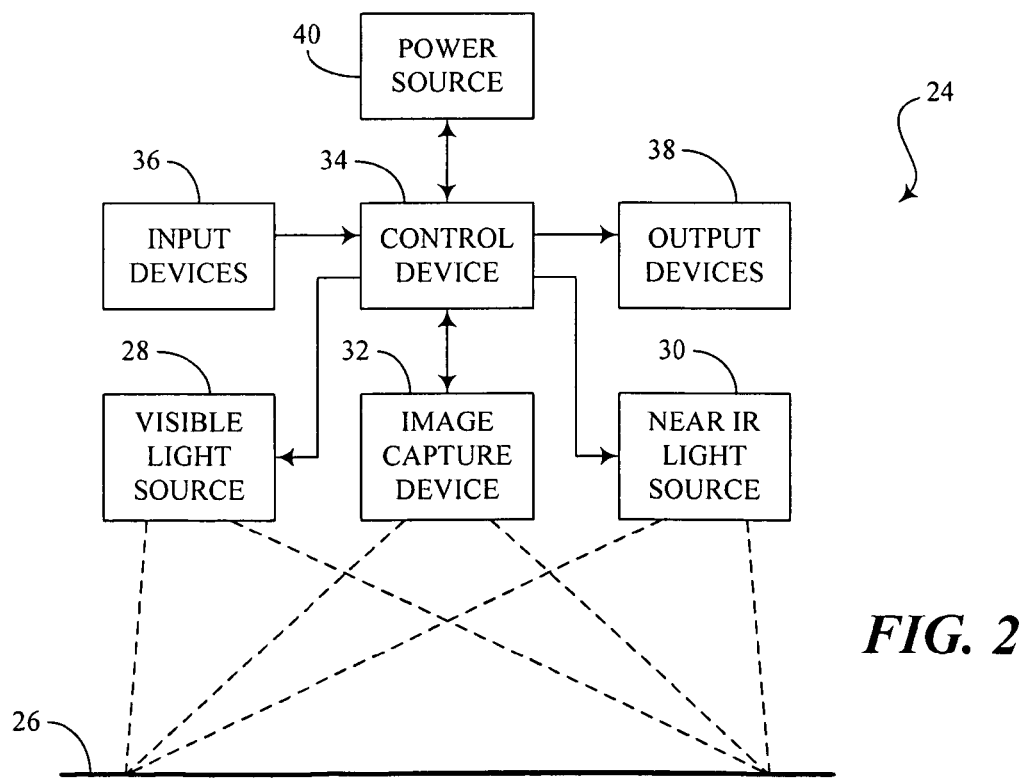
FIG. 2 is a block diagram illustrating blood vessel locating circuitry according to one embodiment.

FIG. 2 is a block diagram illustrating an embodiment of blood vessel locating circuitry 24. Blood vessel locating circuitry 24, for example, can be associated with or incorporated within blood vessel locating device 10 of FIG. 1 or other device for locating blood vessels embedded under a portion of skin 26 of a subject or patient. In this embodiment, blood vessel locating circuitry 24 includes a visible light source 28, near IR light source 30, image capture device 32, control device 34, input devices 36, output devices 38, and power source 40.

Visible light source 28 is adapted to provide light to illuminate a portion of skin 26 of the subject. The light emitted from visible light source 28 is contained within a wavelength spectrum encompassing light waves that are visible to the human eye. For example, the visible light spectrum may include wavelengths ranging from 380 nm to 750 nm. In some embodiments, visible light source 28 comprises one or more light emitting diodes (LEDs) capable of emitting light within a narrow wavelength range. Some LEDs, for instance, can be categorized as having a single wavelength, such as 470 nm for emitting a bluish colored light, 660 nm for emitting a reddish colored light, etc. In other embodiments, visible light source 28 comprises one or more incandescent bulbs that are capable of providing white light making up a wide spectrum of frequencies. Visible light source 28 may include any suitable number and any suitable type of device or devices for emitting light in the visible spectrum.

Near IR light source 30 is adapted to provide light to illuminate substantially the same portion of skin 26 of the subject that is illuminated by visible light source 26. The light emitted from near IR light source 30 is contained within a wavelength spectrum encompassing light waves in the near IR range, which includes infrared light from 700 nm to 1.4 μm. Particularly, near IR light source 30 may be configured using one or more LEDs capable of emitting a light having a narrow wavelength band within the near IR range. In some embodiments, near IR light source 30 may be LEDs configured to emit 880 nm infrared light. In other embodiments, near IR light source 30 may include one or more devices that emit a wide spectrum of frequencies within the near IR range.

Image capture device 32 is arranged in an orientation that allow it to capture at least an area of skin 26 illuminated by the two light sources. Image capture device 32 may include a digital camera, digital video camera, array of CCDs, CMOS devices, or other suitable devices for capturing images of skin 26. Furthermore, image capture device 32 may include one or more lenses, filters, etc., as needed.

Control device 34 manages when visible light source 28 emits light and when near IR light source 30 emits light. In some embodiments, control device 34 may cause visible light source 28 and near IR light source 30 to turn on at alternating times. In this way, skin 26 is illuminated with visible light for a first time period, illuminated with near IR light for a second time period, illuminated with visible light for a third time period, and so on. Control device 34 is further configured to instruct image capture device 32 to capture images of the same portion of skin 26 during the first time period, second time period, third time period, etc., to synchronize the light emission times with the image capturing times. The rate at which the light sources alternate correlates to the number of frames per second that are processed and displayed, which may be based on the processing speed of control device 34 and/or a time required for the light sources to reach a steady or predictable illumination state from an off state.

Images from image capture device 32 are transmitted to control device 34, which then processes the images to locate blood vessels. Particularly, control device 34 individually filters the two different images to prepare the image for further processing. Control device 34 obtains a differential image showing the difference between the two images and then enhances the differential image. The enhanced image is then superimposed on one of the images for display on output device 38.

Control device 34 may be a general-purpose or specific-purpose processor or microcontroller. Control device 34 may be associated with memory, which can include internally fixed storage and/or removable storage media for storing information, data, and/or instructions. Memory can also store one or more software programs that enable control device 34 to execute blood vessel locating programs and procedures as discussed in the present disclosure.

Various logical instructions or commands may be included in the one or more software programs for locating blood vessels. The blood vessel locating programs executed by control device 34 can be implemented in hardware, software, firmware, or a combination thereof. When implemented in software or firmware, the programs can be stored in the memory and executed by control device 34. Blood vessel locating programs or software and any other programs or software code including executable logical instructions as described herein can be embodied in any suitable computer-readable medium for execution by any suitable processing device. The computer-readable medium can include any physical medium that can store the programs or software code for a measurable length of time. When implemented in hardware, the blood vessel locating programs can be implemented, for example, using discrete logic circuitry, an application specific integrated circuit (ASIC), a programmable gate array (PGA), a field programmable gate array (FPGA), etc., or any combination thereof.

Input devices 36 may include any combination of keys, keypads, cursor control devices, switches, buttons, touch screen sensing mechanisms, etc., and/or may include any other suitable mechanisms allowing a user to enter data, instructions, information, etc. Output devices 38 may include any combination of display screens, such as display screen 20, indicator lights, audio mechanisms, etc., and/or may include any other suitable mechanisms for communicating information to the user. Input devices 36 and/or output devices 38 may be on the same physical device as image capture device 32 or alternatively may be separate, as desired. Power source 40 may include any suitable type of battery or batteries, battery related circuitry, rechargeable batteries, regulators, AC adapters, etc., and/or may include any other suitable device for providing electrical power to the components of blood vessel locating circuitry 24.

Figure 3:
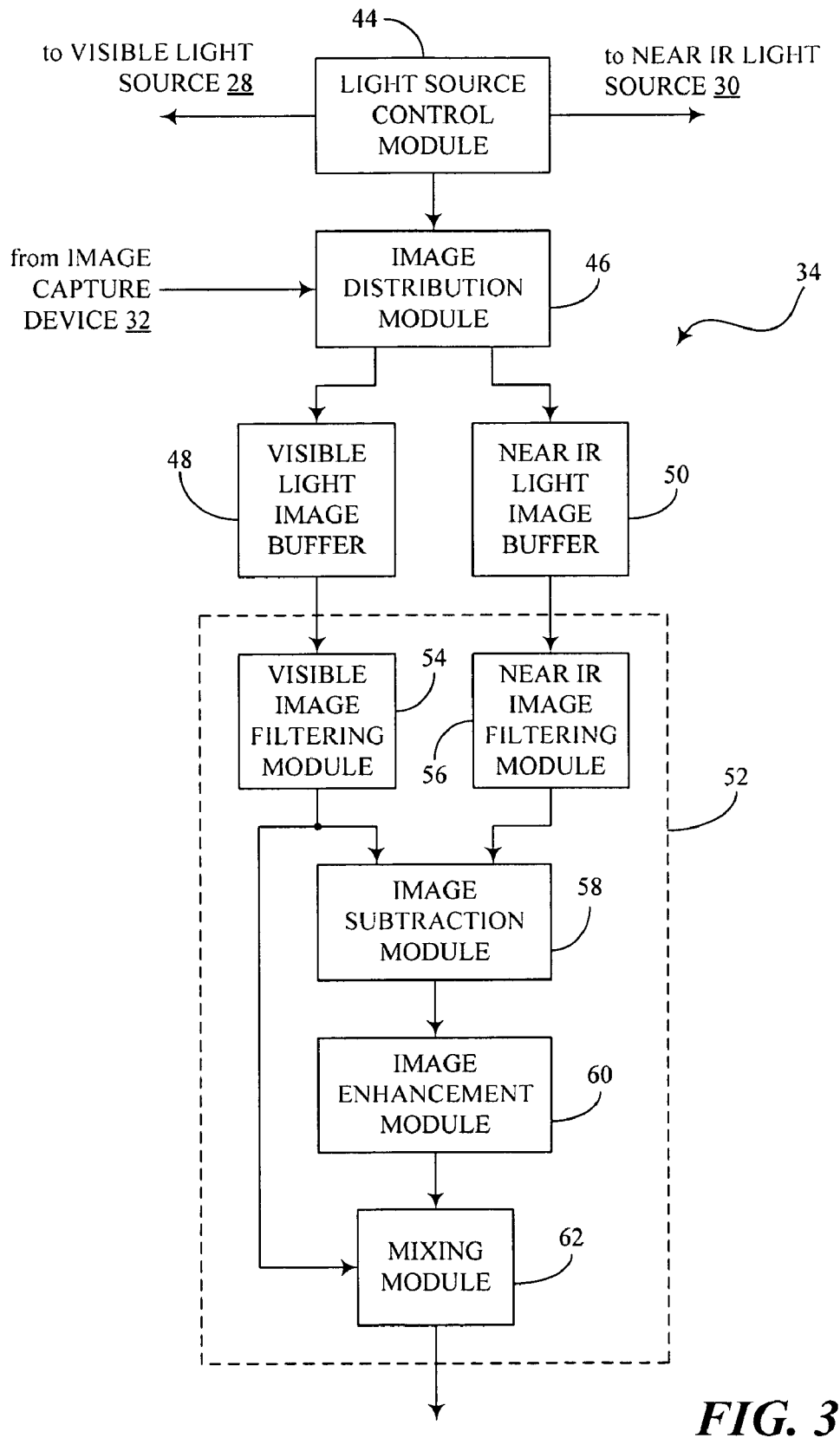
FIG. 3 is a block diagram illustrating the control device shown in FIG. 2 according to one embodiment.

FIG. 3 is a block diagram illustrating an embodiment of control device 34 shown in FIG. 2. In this embodiment, control device 34 includes a light source control module 44, image distribution module 46, visible light image buffer 48, near IR light image buffer 50, and image processing module 52. Image processing module 52 includes a visible image filtering module 54, a near IR image filtering module 56, an image subtraction module 58, an image enhancement module 60, and a mixing module 62. The elements of control device 34 may be embodied in software and/or hardware.

Light source control module 44 may be configured to receive user inputs regarding information with respect to light source usage and times and other input for adjusting timing or clocking characteristics. Based on a predetermined or adjusted timing control pattern, light source control module 44 sends a signal to visible light source 28 as an instruction to emit light for a first period of time. Light source control module 44 also sends another signal to near IR light source 30 as an instruction to emit light for a second period of time. In some embodiments, the first and second periods of time can be the same, but in alternative embodiment, the time periods may be different if desired. These or other output signals from light source control module 44 are also sent to image capture device 32 as instructions to capture images of a portion of a subject's skin when illuminated by visible light source 28 or near IR light source 30. Light source control module 44 sends the signals to the light sources and image capture device 32 to coordinate or synchronize the illumination characteristics with the image capturing functions of image capture device 32. Thus, images of the subject's skin can be adequately obtained when illuminated by the two different light emissions.

Image distribution module 46 is configured to receive images that are captured by image capture device 32. When an image is captured during the time that the subject's skin is illuminated with visible light, image distribution module 46 stores the image in visible light image buffer 48. On the other hand, when an image is captured during the time that the subject's skin is illuminated with near IR light, image distribution module 46 stores the image in near IR light image buffer 50. Buffers 48 and 50 may be configured to store a single image at a time. Therefore, a new image to be stored in a respective buffer replaces or writes over an old image. In other embodiments, buffers 48 and 50 may be configured to stored more than one image. With at least one image in each buffer 48 and 50, image processing module 52 can retrieve the latest images from the two buffers in order to process them according to the image processing description herein.

Image processing module 52 includes visible image filtering module 54, which receives an image from visible light image buffer 48. Visible image filtering module 54 filters the visible image using any suitable filtering or processing techniques to prepare the visible image for further processing. The visible image can be processed to more clearly show features of the subject's skin that may not be as noticeable under other lights. Filtering may include smoothing effects to reduce the view of certain features of the skin, such as hair, freckles, changes in skin pigmentation, etc., the images of which are not necessarily needed for processing so as to help determine blood vessel location.

Near IR filtering module 56 receives an image from near IR light image buffer 50 and filters the image using any suitable filtering or processing techniques to prepare the near IR image for further processing. Filtering in this respect may include enhancing contrast, altering brightness levels, sharpening the edges of the image, etc. Near IR image may be processed to more clearly show features that may not be as apparent under other lights and/or to reduce the view of certain features that are not necessarily needed for processing so as to help determine blood vessel location.

Image subtraction module 58 receives image data relating to a first image from visible image filtering module 54 and simultaneously receives image data relating to a second image from near IR image filtering module 56. Image subtraction module 58 then calculates the differences between the two images, captured at approximately the same time, where each image represents illumination by one of the two sources of different lights. The differences between the two images can be calculated, for example, by subtracting the pixel values of the visible light image from the pixel values of the near IR light image. In other embodiments, image subtraction module 58 may subtract the near IR light image from the visible light image. The resulting image calculated by the difference between the two images is referred to herein as a differential image.

Image enhancement module 60 receives the differential image from image subtraction module 58 and enhances the differential image. Enhancement in this respect may include any suitable processing algorithms or procedures to more greatly distinguish the differences between the two original images. For example, image enhancement module 60 may comprise a colorization procedure to add colors, such as brighter or more noticeable colors, to the differential image. Other examples of enhancement may include adjusting the contrast or brightness of the image. These and other procedures may be run to enhance the differential image. The enhanced image is then sent to mixing module 62. Mixing module 62 combines the enhanced image with the visible light image from visible light image buffer 48. Mixing module 62 combines the images by superimposing one image on the other, using a mixing algorithm, or using any other suitable image combining procedures. At its output, mixing module 62 can provide the final image to an output device, such as, for instance, display screen 20.

Figure 4:
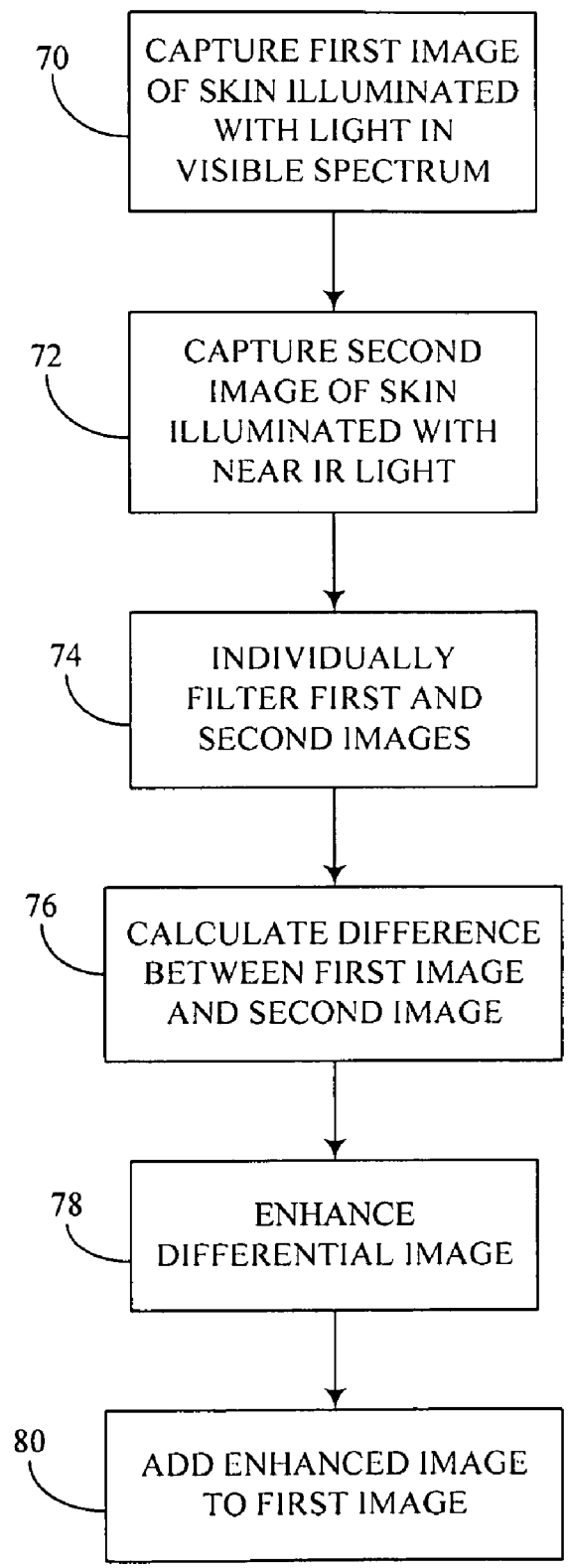
FIG. 4 is a flow chart illustrating a method for locating blood vessels according to one embodiment.

FIG. 4 is a flow chart showing an embodiment of a method for locating blood vessels. As indicated in block 70 shown in this embodiment, a first image of a subject's or patient's skin is captured. The image is captured when the skin is illuminated with light having at least one wavelength in the visible light spectrum. In block 72, a second image of the subject's skin is captured. The capture image in this case is associated with the condition that the skin is illuminated with a light emission within the near IR spectrum. The image capture procedures of blocks 70 and 72 may further be associated with procedures for storing the images as needed. In some embodiments, blocks 70 and 72 may be reversed such that when a current near IR light illuminated image is already stored, the next image to be captured may be a visible light illuminated image.

After two images of the skin are captured and/or stored, as mentioned with respect to blocks 70 and 72, the flow chart proceeds to block 74. As indicated in block 74, each of the first and second images is individually filtered. Filtering may include any suitable procedure or procedures for enhancing or reducing certain features of the images. After individual filtering, a difference is calculated between the first image associated with visible light illumination and the second image associated with near IR light illumination, as indicated in block 76. This subtraction process is performed in order to obtain a differential image. In block 78, the differential image is enhanced using any suitable enhancement technique. In block 80, the enhanced image is added or mixed with the first image associated with visible light illumination to obtain a final image showing an enhanced view of the location of blood vessels.

It should be understood that the steps, processes, or operations described herein may represent any module or code sequence that can be implemented in software or firmware. In this regard, these modules and code sequences can include commands or instructions for executing specific logical steps, processes, or operations within physical components. It should further be understood that one or more of the steps, processes, and/or operations described herein may be executed substantially simultaneously or in a different order than explicitly described, as would be understood by one of ordinary skill in the art.

Figure 5:
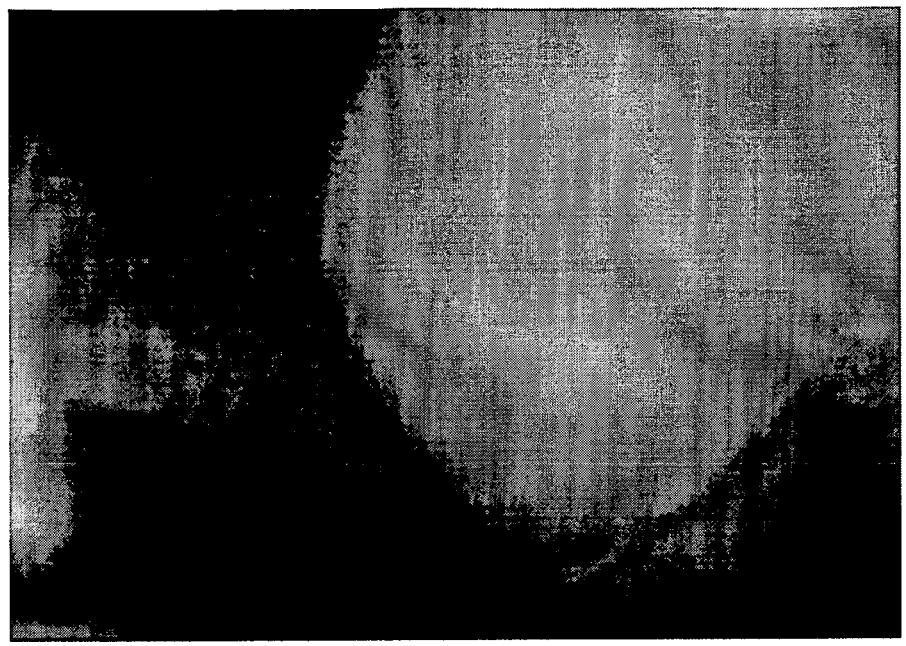
FIG. 5 is an image of a portion of a subject's skin illuminated with light in the visible spectrum, according to one embodiment.
Figure 6:
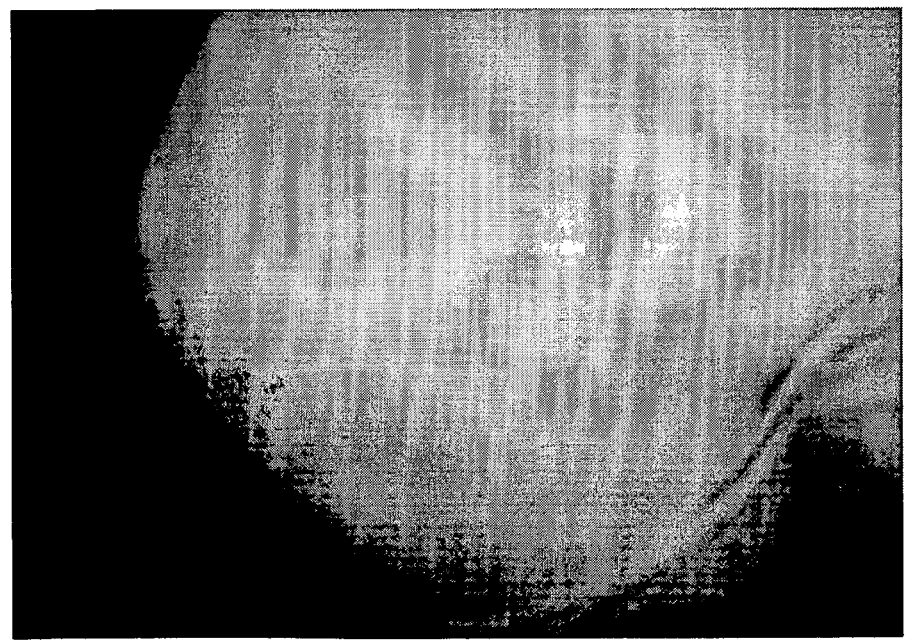
FIG. 6 is an image of a portion of a subject's skin illuminated with light in the near IR spectrum, according to one embodiment.
Figure 7:
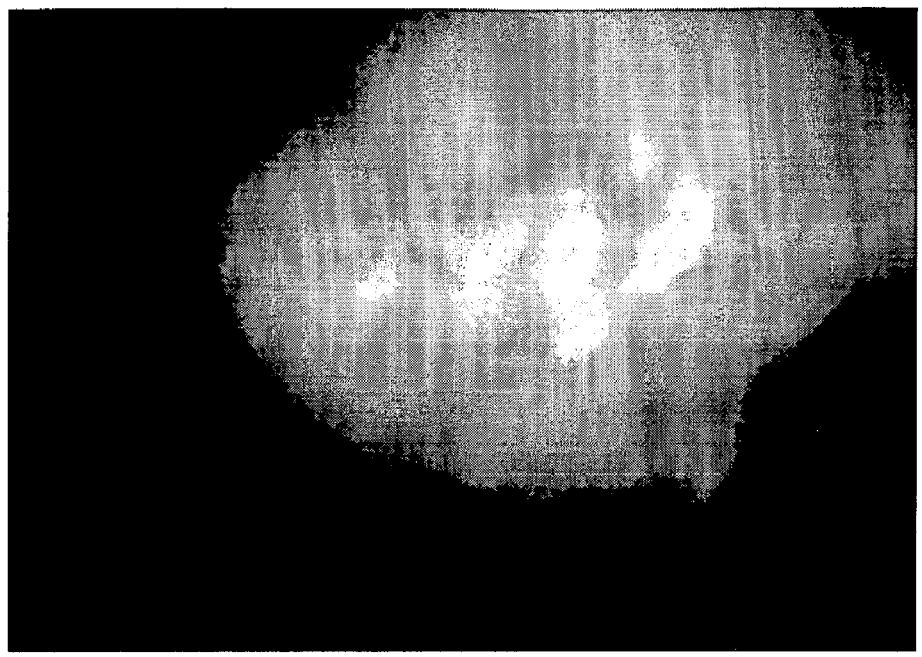
FIG. 7 is a differential image processed by calculating a difference between the image of FIG. 5 and the image of FIG. 6, according to one embodiment.
Figure 8:
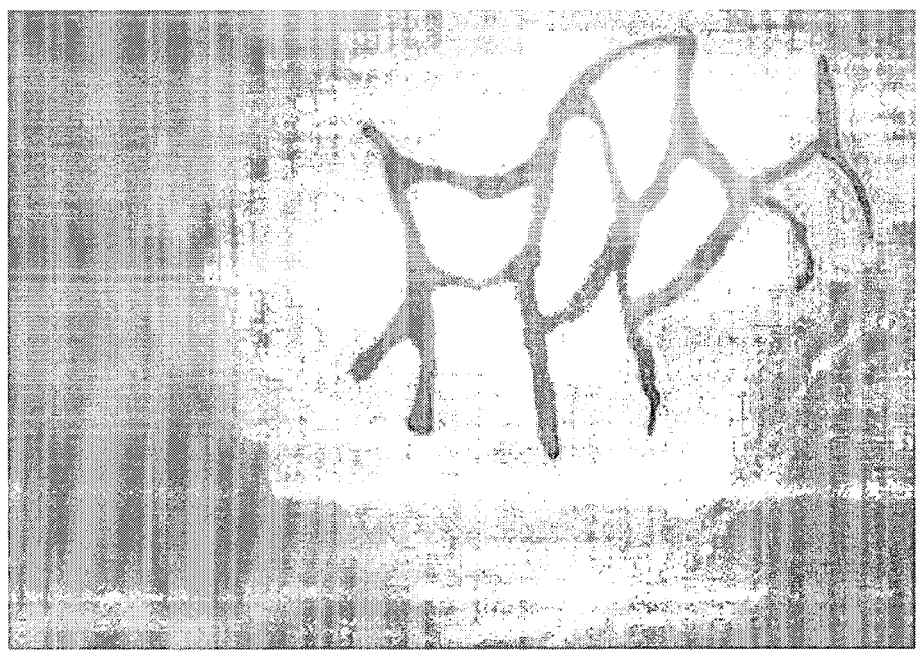
FIG. 8 is an image processed by enhancing the differential image of FIG. 7, according to one embodiment.
Figure 9:
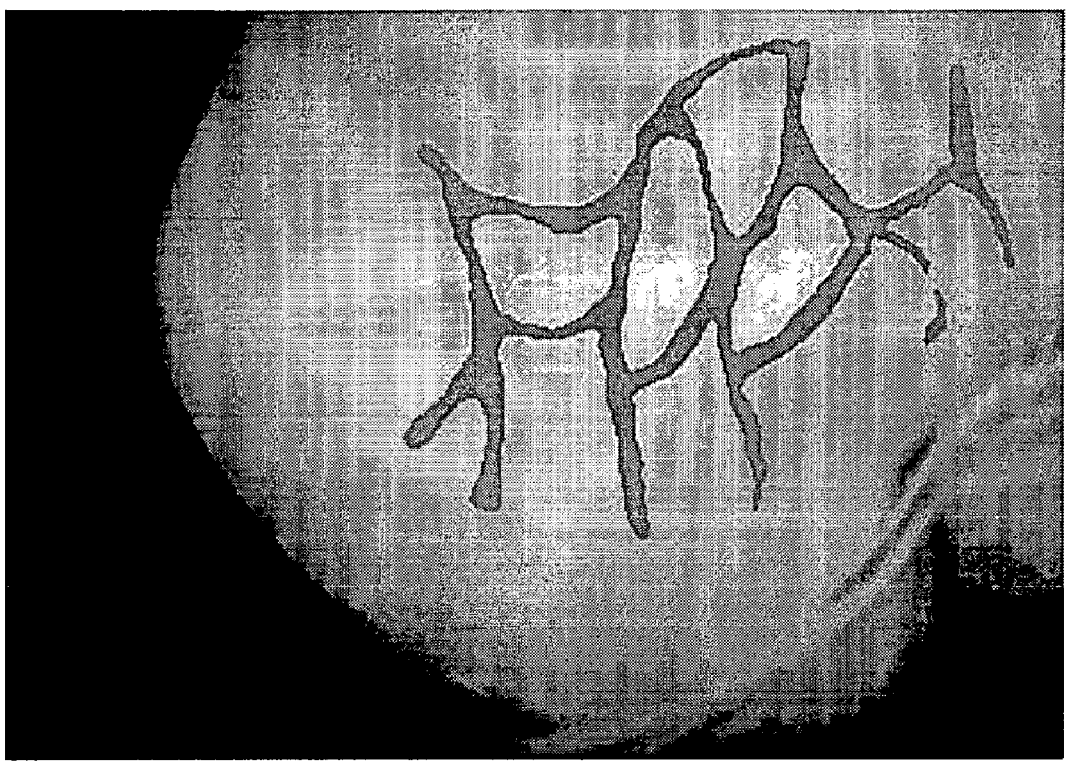
FIG. 9 is an image processed by adding the enhanced image of FIG. 8 with the image of FIG. 5, according to one embodiment.

FIGS. 5-8 show examples of captured images of a portion of a subject's skin. Particularly, FIG. 5 shows an image of the subject's skin when illuminated with light emission in the visible light spectrum. FIG. 6 shows an image of the subject's skin when illuminated with light emission in the near IR light spectrum. From these two captured images, image processing techniques are used to enhance an image that can be displayed for the user to see. FIG. 7 shows a differential image calculated from the difference between the images of FIGS. 5 and 6. In some embodiments, one image, such as the visible light image, is subtracted from the other image, such as the near IR light image. The differential image of FIG. 7 is enhanced to more clearly distinguish the blood vessels from surrounding tissue. The enhanced image is illustrated in FIG. 8. FIG. 9 shows the final image when the enhanced differential image is added back with the visible light image. This final image can be displayed on a display screen for clearly showing the location of blood vessels embedded under the skin. By utilizing the systems and devices described herein, a medical professional can more clearly see the location of blood vessels of a patient and may thus reduce the number of unsuccessful needle probing operations.

The embodiments described herein merely represent exemplary implementations and are not intended to necessarily limit the present disclosure to any specific examples. Instead, various modifications can be made to these embodiments as would be understood by one of ordinary skill in the art. Any such modifications are intended to be included within the spirit and scope of the present disclosure and protected by the following claims.

We claim:

1. A blood vessel locating system comprising:
    an image capture device configured to capture a first image of a region of skin of a subject when the region is illuminated by a first light and to capture a second image of the region of skin when the region is illuminated by a second light; and
    an image processing module configured to calculate the difference between the first image and the second image to obtain a differential image, the image processing module further configured to enhance the differential image to obtain an enhanced image of blood vessels located under the surface of the skin of the subject and to superimpose the enhanced image of the blood vessels on the first image to obtain a final image.

2. The blood vessel locating system of claim 1, further comprising:
    a first light source configured to emit the first light in order to illuminate the region of skin of the subject, the first light having at least one wavelength within a visible spectrum; and
    a second light source configured to emit the second light in order to illuminate the region of skin of the subject, the second light having at least one wavelength within the near infrared spectrum.

3. The blood vessel locating system of claim 2, wherein the first light source is configured to emit a broadband white light.

4. The blood vessel locating system of claim 2, wherein the first light source comprises one or more light emitting diodes (LEDs) configured to emit the first light at a wavelength of approximately 470 nm.

5. The blood vessel locating system of claim 2, wherein the second light source comprises one or more LEDs configured to emit the second light at a wavelength of approximately 880 nm.

6. The blood vessel locating system of claim 2, further comprising:
    an open-ended enclosure, wherein the first light source and second light source reside on an interior surface of the open-ended enclosure.

7. The blood vessel locating system of claim 2, further comprising:
    a control device configured to control when the first light source and the second light source emit light, the control device further configured to synchronize the image capture device to capture the first image when the first light source emits light and to capture the second image when the second light source emits light.

8. The blood vessel locating system of claim 1, wherein the image processing module is further configured to individually filter the first and second images before calculating the difference between the first image and the second image.

9. The blood vessel locating system of claim 1, further comprising:
    a display screen configured to display the final image.

10. The blood vessel locating system of claim 1, wherein the image processing module is configured to enhance the differential image by adding color to the differential image.

11. A control device comprising:
    a first buffer configured to temporarily store a first image of a region of skin of a subject when the region is illuminated with a first light;
    a second buffer configured to temporarily store a second image of the region of skin of the subject when the region is illuminated with a second light;
    an image subtraction module configured to calculate the difference between the first image and the second image to obtain a differential image;
    an image enhancement module configured to enhance the differential image to obtain an enhanced image; and
    a mixing module configured to superimpose the enhanced image on the first image to obtain a final image, wherein the mixing module is further configured to provide the final image to a display screen.

12. The control device of claim 11, further comprising:
    a light source control module configured to control a first light source that emits the first light and to control a second light source that emits the second light.

13. The control device of claim 12, wherein the light source control module causes the first light source and second light source to emit light at alternating time periods.

14. The control device of claim 11, further comprising:
    an image distribution module configured to store images from an image capture device into either the first buffer or the second buffer.

15. The control device of claim 11, further comprising:
    a first filtering module configured to receive the first image from the first buffer and prepare the first image for further processing by the image subtraction module; and
    a second filtering module configured to receive the second image from the second buffer and prepare the second image for further processing by the image subtraction module.

16. The control device of claim 11, wherein the first light comprises at least one wavelength in a visible light spectrum and the second light comprises at least one wavelength in the near infrared light spectrum 17. The control device of claim 16, wherein the first light contains a wavelength of approximately 470 nm and the second light contains a wavelength of approximately 880 nm.

18. A method comprising:
    capturing a first image of a portion of a surface of a subject's skin that is illuminated by a first light within a visible light spectrum;
    filtering the first image;
    capturing a second image of the portion of the surface of the subject's skin illuminated by a second light within a near infrared light spectrum;
    filtering the second image;

calculating the difference between the filtered first image and the filtered second image to obtain a differential image;

enhancing the differential image to obtain an enhanced image; and adding the enhanced image with either of the filtered first image or the filtered second image to obtain a final image.

19. The method of claim 18, wherein the visible light spectrum spans a range from about 380 nm to about 750 nm.

20. The method of claim 19, wherein the first light comprises a wavelength of approximately 470 nm.

21. The method of claim 18, wherein the second light comprises a wavelength of approximately 880 nm.

22. The method of claim 18, wherein filtering the first and second images comprises optimizing at least a first feature of the image or minimizing at least a second feature of the image.

23. The method of claim 18, wherein enhancing the differential image comprises colorizing the differential image, adjusting the contrast of the differential image, and/or darkening the differential image.

* * * * *